United States Patent
Jing et al.

(10) Patent No.: US 10,026,162 B2
(45) Date of Patent: Jul. 17, 2018

(54) METHOD AND DEVICE FOR SEALANT COATING INSPECTION

(71) Applicants: BOE TECHNOLOGY GROUP CO., LTD, Beijing (CN); HEFEI BOE OPTOELECTRONICS TECHNOLOGY CO., LTD., Hefei (CN)

(72) Inventors: Yangkun Jing, Beijing (CN); Jia Ding, Beijing (CN); Xiaopan Che, Beijing (CN); Haibo Li, Beijing (CN)

(73) Assignees: BOE TECHNOLOGY GROUP CO., LTD., Beijing (CN); HEFEI BOE OPTOELECTRONICS TECHNOLOGY CO., LTD., Hefei (CN)

( * ) Notice: Subject to any disclaimer, the term of this patent is extended or adjusted under 35 U.S.C. 154(b) by 198 days.

(21) Appl. No.: 15/030,977

(22) PCT Filed: Dec. 8, 2015

(86) PCT No.: PCT/CN2015/096663
§ 371 (c)(1),
(2) Date: Apr. 21, 2016

(87) PCT Pub. No.: WO2016/091152
PCT Pub. Date: Jun. 16, 2016

(65) Prior Publication Data
US 2016/0343122 A1    Nov. 24, 2016

(30) Foreign Application Priority Data

Dec. 8, 2014 (CN) .......................... 2014 1 0746965

(51) Int. Cl.
*G06T 7/00* (2017.01)
*G01N 21/84* (2006.01)
(Continued)

(52) U.S. Cl.
CPC .......... *G06T 7/0004* (2013.01); *G01N 21/84* (2013.01); *G01N 21/8422* (2013.01);
(Continued)

(58) Field of Classification Search
CPC ........ G06T 7/0004; G06T 2207/30121; G01N 21/84; G01N 21/8422; G01N 21/8851;
(Continued)

(56) References Cited

U.S. PATENT DOCUMENTS

2005/0140911 A1    6/2005  Ryu et al.
2016/0025649 A1*   1/2016  Lee .......................... G06T 11/60
                                                              382/147

FOREIGN PATENT DOCUMENTS

CN    101001521      *   7/2007
CN    101001521   A       7/2007
(Continued)

OTHER PUBLICATIONS

The State Intellectual Property Office of the People's Republic of China (SIPO) Office Action 1 for 201410746965.5 dated Jun. 22, 2016 p. 1-8.
(Continued)

*Primary Examiner* — Thai Tran
*Assistant Examiner* — Christopher T Braniff
(74) *Attorney, Agent, or Firm* — Anova Law Group, PLLC (57) ABSTRACT

The present disclosure provides a method and a device of inspecting a sealant coating on a substrate. An image of a sample substrate is captured. The sample substrate is selected from a plurality of substrates. A non-coating area is identified from the image of the sample substrate. Abnormal points are identified in the non-coating area. Positions of the abnormal points are recorded. An image of a sealant-coated substrate having a sealant coating on one of the plurality of
(Continued)

substrates is captured. Defect positions of the sealant coating are identified from the image of the sealant-coated substrate. Defects located in a non-coating area of the sealant-coated substrate at positions corresponding to the positions of the abnormal points identified based on the sample substrate are considered as normal.

18 Claims, 3 Drawing Sheets

(51) Int. Cl.
*G01N 21/88* (2006.01)
*G01N 21/95* (2006.01)
*G06K 9/46* (2006.01)
*G06K 9/62* (2006.01)
*H04N 5/225* (2006.01)
*H04N 5/372* (2011.01)

(52) U.S. Cl.
CPC ....... *G01N 21/8851* (2013.01); *G06K 9/4661* (2013.01); *G06K 9/6267* (2013.01); *H04N 5/2256* (2013.01); *H04N 5/372* (2013.01); *G01N 2021/8427* (2013.01); *G01N 2021/8433* (2013.01); *G01N 2021/8887* (2013.01); *G01N 2021/9513* (2013.01); *G06T 2207/30121* (2013.01)

(58) Field of Classification Search
CPC ... G01N 2021/8427; G01N 2021/8433; G01N 2021/8887; G01N 2021/9513; G06K 9/4661; G06K 9/6267; H04N 5/2256; H04N 5/372
See application file for complete search history.

(56) References Cited

FOREIGN PATENT DOCUMENTS

| | | |
|---|---|---|
| CN | 101556384 A | 10/2009 |
| CN | 101676774 A | 3/2010 |
| CN | 102368130 A | 3/2012 |
| CN | 103134785 A | 6/2013 |
| CN | 103170434 A | 6/2013 |
| CN | 203124215 U | 8/2013 |
| CN | 203454973 U | 2/2014 |
| CN | 104359915 A | 2/2015 |
| JP | H08334478 A | 12/1996 |
| TW | I278054 B | 4/2007 |
| WO | 2014163375 A1 | 10/2014 |

OTHER PUBLICATIONS

The World Intellectual Property Organization (WIPO) International Search Report for PCT/CN2015.096663 dated Mar. 1, 2016.

* cited by examiner

METHOD AND DEVICE FOR SEALANT COATING INSPECTION

CROSS-REFERENCES TO RELATED APPLICATIONS

This application is a national phase entry under 35 U.S.C. § 371 of International Application No. PCT/CN2015/096663, filed on Dec. 8, 2015, which claims priority to Chinese Patent Application No. CN201410746965.5, filed on Dec. 8, 2014. The above enumerated patent applications are incorporated by reference herein in their entirety.

FIELD OF THE DISCLOSURE

The present disclosure generally relates to the field of display technologies and, more particularly, relates to a sealant coating inspection method and a device thereof.

BACKGROUND

In making of a liquid crystal display (LCD) device, sealant materials are often coated and cured in the periphery of an array substrate or a color filter substrate. The sealant material is used to bond the array substrate and the color filter substrate together and to protect the liquid crystals injected into the space between the array substrate and the color filter substrate from being affected by the ambient air and water.

Figure 1:
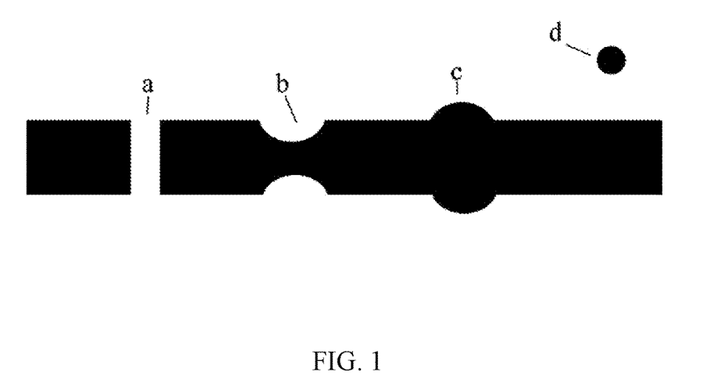
FIG. 1 illustrates various forms of defects of a sealant coating.

After the array substrate or the color filter substrate is coated with the sealant material, the sealant coating needs to be inspected to detect any occurrences of defects such as a crack or gap ("a" as shown in FIG. 1), a non-uniform line (too thin "b" and too thick "c" as shown in FIG. 1), a spilled drop ("d" as shown in FIG. 1), etc.

In a conventional process, the sealant coating is inspected as follows. In a first step, one or more mark points are configured on the array substrate or the color filter substrate coated with the sealant material. The mark points are usually patterns clearly identifiable in terms of brightness and/or contrast difference under certain pre-configured lighting condition. The sealant material is coated in a graphic pattern to maintain certain position relationship with the mark points. In a second step, an image acquisition unit, e.g., a charge-coupled device (CCD) camera, is used to capture images of the array substrate or the color filter substrate coated with the sealant material under certain pre-configured lighting condition. In a third step, due to the brightness and/or contrast difference, the mark points are easily identifiable from the captured images and the identified positions of the mark points have very small deviations from the actual positions. Based on the relationship between the mark points and the graphic pattern of the sealant coating, the identified positions of the mark points are used to determine the ideal graphic pattern of the sealant coating in the captured images.

In the meantime, the actual graphic pattern of the sealant coating is determined based on the brightness and/or contrast difference. In a fourth step, the actual graphic pattern of the sealant coating from the captured images and the ideal graphic pattern of the sealant coating determined by the mark points are compared to detect any occurrences of defects such as cracks, gaps, non-uniform lines and spilled drops of the coated sealant.

However the above described inspection process has the following drawbacks. Firstly, gate lines, data lines, and other signal lines, thin film transistors, pixel electrodes and other structures are usually formed on the array substrate. Color filters, black matrix, etc. are usually formed on the color filter substrate. These structures may also be captured in the images, may interfere with the mark points, and may cause errors in identifying the mark points and in forming the ideal graphic pattern of the sealant coating. In addition, these structures may also interfere with the actual graphic pattern of the sealant coating when being identified. The area that does not include the sealant coating may be undesirably recognized as being coated with the sealant material, which includes over-identification or false identification. On the other hand, the area that does include the sealant coating may not be recognized as being coated with the sealant material, which includes under-identification. Thus, the inspection results have significant deviations and are considered as unreliable.

Secondly, due to the frequent occurrences of the over-identifications and under-identifications in the inspection results, on-site human intervention is required to refine the parameters of the sealant coating process. Thus, more time is then needed and the productivity of the sealant coating process is reduced.

Finally, the above inspection process of the sealant coating does not assure the pre-configured lighting condition of the light sources, nor monitors the status of the image acquisition unit. When the substrate illumination changes, for example, the light intensity of the light sources decreases over time, the image acquisition unit is out of focus, and/or the lens transmittance fluctuates, for example, dust is accumulated on the lens surface of the CCD camera. The captured images may not accurately reflect the actual graphic pattern of the sealant coating. Thus, the inspection result concluded from the captured images is unreliable.

The disclosed method and device for sealant coating inspection are directed to at least partially solve one or more problems set forth above and other problems in the art.

BRIEF SUMMARY OF THE DISCLOSURE

One aspect of the present disclosure provides a method of sealant coating inspection. An image of a sample substrate is captured. The sample substrate is selected from a plurality of substrates. A non-coating area is identified from the image of the sample substrate. Abnormal points are identified in the non-coating area. Positions of the abnormal points are recorded. An image of a sealant-coated substrate having a sealant coating on one of the plurality of substrates is captured. Defect positions of the sealant coating are identified from the image of the sealant-coated substrate. Defects located in a non-coating area of the sealant-coated substrate at positions corresponding to the positions of the abnormal points identified based on the sample substrate are considered as normal.

Optionally, a group of sample substrates is selected from the plurality of substrates, and the group of sample substrates includes the sample substrate. Images of the group of sample substrates are captured. Abnormal points in non-coating areas of the group of sample substrates are identified. A combination of the abnormal points from the images of the group of sample substrates is considered as normal for identifying the defect positions of the sealant coating of the sealant-coated substrate.

Optionally, the image of the sample substrate is repeatedly captured to obtain a plurality of images of the sample substrate. The abnormal points include a combination of abnormal points from each image of the plurality of images of the sample substrate.

Optionally, prior to the step of identifying the non-coating area from the image of the sample substrate, brightness and contrast of the image of the sample substrate are examined to determine whether the brightness and the contrast is each within a pre-configured range. The non-coating area is identified from the image of the sample substrate, when the brightness and the contrast is each within a pre-configured range.

Optionally, a light source is configured on at least one side of the sample substrate or the sealant-coated sample substrate for illumination. Optionally, a light source is configured on each of opposing sides of the sample substrate or the sealant-coated sample substrate for illumination.

Optionally, a light intensity of the light source is monitored. Optionally, mark points are configured on the sample substrate. The non-coating area is identified by examining a position of an alignment pattern containing the mark points and based on a relationship between positions of the mark points and a coating area supposed for coating the sealant material, to identify the coating area supposed for the sealant coating. The non-coating area is outside of the coating area.

Optionally, at least two mark points are configured on the sample substrate. Optionally, when identifying the abnormal points in the non-coating area, brightness and contrast characteristics of the sealant coating are acquired and compared with brightness and contrast characteristics of the image of the sample substrate in the non-coating area. When the brightness and contrast characteristics of certain areas or points in the image of the sample substrate have substantially same brightness and contrast characteristics of the sealant coating, the certain areas or points are identified as the abnormal points.

Another aspect of the present disclosure provides a device for sealant coating inspection including an image acquisition unit, an abnormal-point identification unit, and a coating defect analysis unit. The image acquisition unit is configured to capture an image of a sample substrate selected from a plurality of substrates. The abnormal-point identification unit is configured to identify a non-coating area from the image of the sample substrate, to identify abnormal points in the non-coating area, and to record positions of the abnormal points. The coating defect analysis unit is configured to identify defect positions of a sealant coating from an image of a sealant-coated substrate having the sealant coating on one of the plurality of substrates. Defects located in a non-coating area of the sealant-coated substrate at positions corresponding to the positions of the abnormal points identified based on the sample substrate are considered as normal.

Optionally, light sources are configured to illuminate the sample substrate or the sealant-coated substrate for inspection. Optionally, the light sources include first light source components and second light source components, configured on opposing sides of the sample substrate or the sealant-coated substrate for inspection.

Optionally, a light source monitoring unit is configured to measure and monitor a light intensity of the light sources. Optionally, a transmittance monitoring unit is configured to measure and monitor a lens surface transmittance of the image acquisition unit.

Optionally, a pre-treatment control system is further configured to analyze the image of the sealant coating and to identify mark points on the sealant-coated substrate corresponding to mark points configured on the sample substrate.

Optionally, the pre-treatment control system includes one or more selected from a CCD system configuration unit, a mark point configuration unit, an imaging system configuration unit, a light source system configuration unit, a light source parameter configuration unit, an image processing unit, a coating platform control unit, and a status recording unit.

Other aspects of the present disclosure can be understood by those skilled in the art in light of the description, the claims, and the drawings of the present disclosure.

BRIEF DESCRIPTION OF THE DRAWINGS

The following drawings are merely examples for illustrative purposes according to various disclosed embodiments and are not intended to limit the scope of the present disclosure.

DETAILED DESCRIPTION

Reference will now be made in detail to exemplary embodiments of the disclosure, which are illustrated in the accompanying drawings. Wherever possible, the same reference numbers will be used throughout the drawings to refer to the same or like parts. It should be understood that the exemplary embodiments described herein are only intended to illustrate and explain the present invention and not to limit the invention.

The present disclosure provides a method and a device of inspecting a sealant coating on a substrate for various defects to reduce the rate of false defect identification and to improve the precision and reliability of the coating inspection results.

Figure 2:
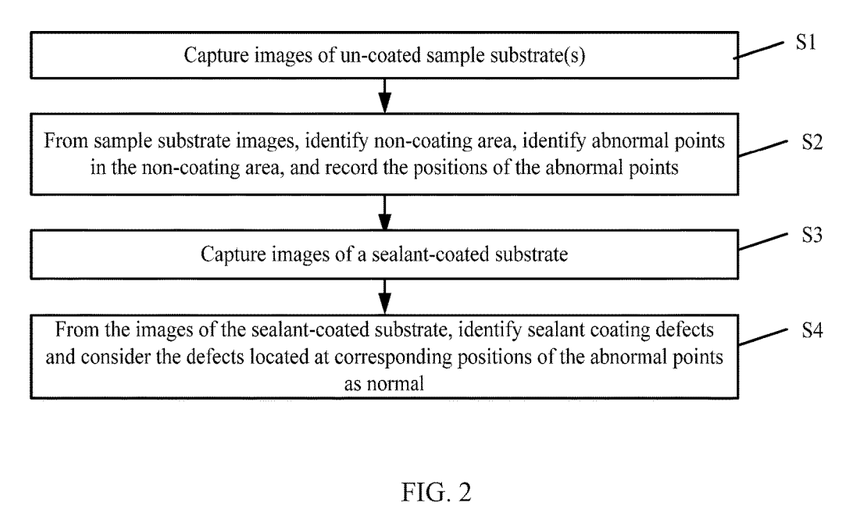
FIG. 2 illustrates a flow chart of an exemplary method of inspecting a sealant coating according to an exemplary embodiment of the present disclosure.

FIG. 2 illustrates a flow chart of an exemplary method of inspecting the sealant coating according to an exemplary embodiment of the present disclosure. In one embodiment, the inspection method is used to detect defects of sealant coating on the substrate. The method includes the following exemplary steps.

In Step S1 of FIG. 2, an image of a sample substrate, i.e., a non-coated sample substrate, is captured before being coated with sealant materials.

For example, before a batch of substrates is coated with the sealant material, one or more sample substrates are selected from the batch of substrates. The images of the sample substrate(s) are captured by an image acquisition unit, for example, a CCD camera. In various embodiments, at least one sample substrate is selected from each batch of substrates.

In Step S2 of FIG. 2, the image of the sample substrate is examined to identify the non-coating area, to recognize any abnormal points in the non-coating area, and to record the positions of the abnormal points.

An alignment pattern containing one or more mark points may be formed on the substrates to be coated, from which the sample substrates are selected. Substrates in a same batch may have the same number of mark points arranged at same positions in the alignment pattern of each substrate. The alignment pattern containing mark points may be in a shape of filled circle, hollow circle, filled cross, hollow cross, or any other suitable shapes that are clearly recognizable and will not be confused with other structures formed on the same substrate.

In Step S2, the alignment pattern containing mark points may be recognized according to the sample substrate images to determine the positions of the mark points in the images. Then, based on the relationship between the positions of the mark points in the alignment pattern with respect to an ideal coating area that sealant material(s) are supposed to be coated thereon, the coating area and the non-coating area may then be determined. In some cases, such relationship between the positions of the mark points in the alignment pattern with respect to the ideal coating area may be obtained during the time when the mark points are formed on the substrates.

In certain embodiments, at least two mark points may be included in each alignment pattern to more precisely recognize the non-coating area, and the abnormal points in the non-coating area from the captured images.

Components or structures may be formed on the substrate in the non-coating area. Such components/structures may include, for example, gate lines, data lines, signal lines, thin film transistors, pixel electrodes, color filters, black matrix, etc. These components may have the brightness and contrast similar or comparable with the brightness and contrast of the sealant coating on the substrate. When the sealant coating is inspected, these components may be undesirably, mistakenly recognized as spilled sealant drops of abnormal dripping of the sealant materials, which may be fed back to the coating production line to cause frequent unnecessary disruptions and adjustments of the sealant coating production line.

As used herein, the term "abnormal points" as described in Step S2 may include: areas/points on the substrate that include above-described mistakenly recognized components and any other areas/points that may possibly be mistakenly recognized or otherwise cause false recognition. The abnormal points may thus be fake sealant drops, e.g., due to mistakenly recognized components.

To identify abnormal points, in one example, the brightness and contrast characteristics of a sealant coating on a substrate are acquired. Then, the brightness and contrast characteristics of the images of the un-coated sample substrate in each of the non-coating area and the coating area supposed for coating sealant materials, are analyzed and then compared with the previously acquired brightness and contrast characteristics of the sealant coating on the substrate, to identify abnormal points. For example, by comparison, when the brightness and contrast characteristics of certain points in the images of the un-coated sample substrate have substantially the same brightness and contrast characteristics of the acquired sealant coating, these certain points may be determined as abnormal points. Positions of the determined abnormal points with respect to the mark points of the alignment pattern may then be calculated and recorded.

In Step S3 of FIG. 2, after sealant materials are coated on one or more substrates selected from the batch of substrates to form sealant-coated substrates, images of the sealant-coated substrates are captured. Specifically, after the Step S2, the substrates are coated with the sealant material. Then images are captured by the image acquisition unit, such as a CCD camera, from the sealant-coated substrates.

It should be noted that substrate(s) selected from the batch of substrates for coating sealant materials for inspection may include any substrate in a same batch that includes the sample substrate. In a specific embodiment, the substrate coated with the sealant material for inspection may be the sample substrate used for identifying abnormal points as described in Steps S1-S2 of FIG. 2.

In Step S4 of FIG. 2, sealant coating defects are recognized from images of the sealant-coated substrate and positions of the identified defects are calculated and recorded. For example, defects located in a non-coating area of the sealant-coated substrate at positions corresponding to the positions of the abnormal points identified based on the sample substrate are considered as normal and may be ignored.

Specifically, positions of the mark points may be identified from images of the sealant-coated substrate. Based on the relationship between the positions of the mark points and the ideal coating area supposed for coating the sealant material, the ideal coating area supposed for coating the sealant material may be determined.

By analyzing the brightness and contrast characteristics of images of the sealant-coated substrate, actual sealant-coated area may be identified. Then, the actual sealant-coated area may be compared to the ideal coating area supposed for coating the sealant material. When the actual sealant-coated area is missing in a width direction of the ideal coating area supposed for coating the sealant material at certain positions, a crack or gap defect is determined at these positions. When the actual sealant-coated area has a line width less than the ideal coating area supposed for coating the sealant material at certain positions, a thin line defect is determined. When the actual sealant-coated area has a line width greater than the ideal coating area supposed for coating the sealant material at certain positions, a thick line defect is determined at these positions. When the actual sealant-coated area is found outside of the ideal coating area supposed for coating the sealant material at certain positions, spilled drop defect is determined. When certain defects are located at the positions abnormal points as identified in Step S2, these defects are considered as false identifications and are removed from defect position output data.

In addition, to reduce the overall production defect rate, in this step, images of thin film transistors, electrodes, and other components/structures formed on the substrate may be inspected to detect any possible defects of thin film transistors, electrodes, and other components/structures, themselves.

After sealant coating defects are detected, the defect type and position data are output to the sealant coating production line to accordingly make adjustments to the sealant coating conditions in the subsequent coating process of remaining substrates in a same batch. For example, when a thick line defect occurs at a certain position, the nozzle pressure of the sealant coating machine may be reduced when the substrate is coated at the position of the defect. Thus, the line width of the sealant coating at the position may be reduced to eliminate the thick line defect.

Note that when the Steps S1-S2 are not included in the inspection method, the Step S3 may be performed directly. A batch of substrates may be coated with the sealant material. The sealant-coated substrates are then inspected. When certain components/structures and the sealant coating have little differences in brightness and contrast, during inspection, such components/structures may be falsely identified as spilled drop defects.

As disclosed, Steps S1-S2 are added before Step S3. The positions of areas/points that may cause false defect identifications are recorded. When the same batch of substrates is inspected, detected defects or abnormal points having same positions with the recorded abnormal points such as fake sealant drops identified in Step S2 may be ignored or removed from consideration. The false defect identifications may be eliminated by inspecting and excluding inferences from the gate lines, data lines, signal lines, thin film transistors, pixel electrodes, color filters, black matrix, common electrodes, and any other components/substrates formed on the substrate before the substrate is coated with the sealant. Additionally, the rate of false defect identifications may be reduced in the process of inspecting the sealant coating. Thus, the precision and reliability of the inspection results may be improved.

Practically, only a portion of abnormal points such as fake sealant drops may be recognized from one sample image of an uncoated substrate due to the variations in sample image brightness and contrast or other problems in identifying fake sealant drops. In one embodiment, multiple sample images are captured in Step S1. Each image is inspected for fake sealant drops to identify as much fake sealant drops as possible. Ideally all positions that may cause false defect identifications may be identified to reduce the chance of missing any fake sealant drops. Thus, the rate of false defect identifications may be further reduced in the process of inspecting the sealant coating.

Specifically, in Step S1, multiple substrates may be selected as sample substrates. Multiple images may be captured from these sample substrates. In Step S2, the output data may include the positions of the fake sealant drops collected from multiple sample images. In addition, only one sample substrate may be selected. Multiple sample images may be captured repeatedly from the same sample substrate. In Step S2, the output data may include the positions of the fake sealant drops collected from multiple sample images.

Specifically, the method of inspecting the sealant coating may also include the following exemplary steps. Before performing Step S2, the sample images may be examined to determine whether the brightness and contrast are within a pre-configured range. When the brightness and contrast of the sample images are within the pre-configured range, the contour of each graphic pattern in the sample images may precisely reflect the actual contour of the graphic pattern of structures formed on the substrate. In this case, Step S2 is performed. When the brightness and contrast of the sample images are not within the pre-configured range, the contour of each graphic pattern in the sample images may significantly deviate from the actual contour of the graphic pattern of structures formed on the substrate. In this case, even if the inspection process continues, the inspection result may be imprecise and unreliable. Thus, the inspection process terminates.

Specifically, light sources may be configured on at least one side of the substrate to illuminate the substrate under inspection to satisfy the pre-configured lighting conditions. Thus, the sample substrate images may have desirable brightness and contrast. Preferably, light sources may be configured on both sides of the substrate. For example, light sources may be configured at the front side of the substrate (facing toward the image acquisition unit) to illuminate the substrate. Light reflected by the substrate may be captured by the image acquisition unit. Light sources may be configured at the rear side of the substrate to illuminate the substrate. Light passing through the substrate may be captured by the image acquisition unit. Compared with a configuration having only the front or rear side, the double side light source configuration enhances the brightness and contrast of the substrate and avoids the highlighted areas of intense brightness. Thus, the mark points in the alignment pattern, actual sealant-coated area and the graphic patterns of other structures may be conveniently recognized from the sample substrate images captured by the image acquisition unit and the graphic patterns of other structures may have more precise contours.

In the conventional inspection process, light sources may be replaced regularly to avoid the fading of the brightness and contrast of the substrate due to the light source aging. Practically, the light intensity of light sources may have been significantly degraded before being replaced. The degraded brightness and contrast of the substrate make it impossible to identify the mark points and the patterns of other structures from the captured images. Or the recognized pattern deviates so significantly from the actual pattern that the inspection process may not continue properly or the inspection result becomes unreliable. Meanwhile, the light intensity of light sources may not be degraded before being replaced. Replacement of still-usable light sources causes waste.

In one embodiment, the method of inspecting the sealant coating also includes monitoring the light intensity of light source. The measurement of the light intensity of light source is constantly acquired. On one hand, when the significant reduction in the light intensity of light source is detected, light source may be immediately replaced to avoid less desirable brightness and contrast of the substrate. On the other hand, light source may be fully utilized to avoid waste and save cost.

In the method of inspecting the sealant coating according to the present disclosure, before the substrates are coated with the sealant material, sample substrate images are examined to identify any fake sealant drops in the non-coating area. After the substrates are coated with the sealant material, the sealant-coated substrate images are examined to identify sealant coating defects. When sealant coating defects are found at the positions of the abnormal points such as fake sealant drops previously identified, such defects may be ignored to reduce the rate of false defect identifications in the process of inspecting sealant coating and to improve the precision and reliability of the sealant coating inspection results. In the meantime, the reduction in the rate of false defect identifications reduces the chance of disruptions to the sealant coating production line, avoids unnecessary adjustments to sealant coating process conditions, and improves the productivity of the sealant coating production line.

In one embodiment, the method of inspecting the sealant coating includes the following exemplary steps. For example, in Step 101: sealant coating platform parameters are configured. Step 102: the control mode of each axis of the sealant coating platform, proportional-integral-derivative (PID) controller parameters, sealant coating resolution, electronic gear, speed, acceleration time, de-acceleration time, etc. are configured. In Step 103: the number of mark points and positions of each mark point are configured. Parameters of alignment pattern of the mark point including detection condition and size are configured. The alignment pattern of the mark point is stored.

In Step 104: the substrate is place on the sealant coating platform. In Step 105: the focus and lens surface transmittance of each camera are configured. In Step 106: the light intensity of light sources is configured. In Step 107: dust setting of light sources and light illumination level of light sources are configured to simulate the on-site light sources for the sealant coating inspection and mark point identification.

In Step 108: sealant coating resolution and the maximum sealant coating cross sectional area are configured. In Step 109: mark point images are captured. In Step 110: sample substrate images are processed for the subsequent steps. In Step 111: the alignment pattern of the mark point stored in Step 103 is used to search for mark points in the sample substrate images. If no match is found, the mark point search fails and the process jumps to Step 113. Otherwise, the process continues to Step 112.

In Step 112: the center coordinate of the detection condition of the mark point images captured in Step 109 is calculated to find the deviation from the center coordinate of the detection condition of the alignment pattern of the mark points stored in Step 103.

In Step 113: the position where the sample substrate is placed is adjusted. Due to the failure to identify the mark points in Step 111, the mark points are absent in the mark point images captured in Step 109. The sample substrate is placed out of range in Step 104. If the decision is to adjust the position where the sample substrate is placed, then the process jumps to Step 104. Otherwise, the process continues to Step 114.

In Step 114: a place holder is provided for the process. In Step 115: the position deviation calculated in Step 112 is converted to the distances the sealant coating platform needs to move in each axis. In Step 116: the distances for movement in each axis obtained in Step 115 are compared to sealant coating resolution configured in Step 108. If the movement distance of an axis is within the sealant coating resolution, the process continues to Step 117. Otherwise, the process jumps to Step 118.

In Step 117, the sealant coating completion notification is prompted. Then the process jumps to Step 114. In Step 118: the sealant coating cross sectional area is checked to determine whether the maximum is reached. The traces and durations of each axis movement between Step 109 and Step 118 are recorded and treated as one operation of sealant coating. If the maximum sealant coating cross sectional area is reached, the process continues to Step 119.

In Step 119: the notification of reaching the maximum sealant coating cross sectional area is prompted. At this point, the maximum number of sealant coating operations configured in Step 108 is reached. However the sealant coating resolution configured in Step 108 is not reached. The sealant coating fails. The process jumps to Step 114.

To inspect sealant coating images and search for mark points, the pre-processing control method further includes the following. The number of mark points configured in Step 103 should be equal to the number of cameras inspecting sealant coating and searching for the mark points. In Step 104, the sample substrate placement position may be configured by the horizontal axis movement, the vertical axis movement and the rotational axis movement or by dragging the mouse pointer. The maximum sealant coating cross sectional area configured in Step 108 is used to limit the number of sealant coating operations. If the maximum sealant coating cross sectional area is reached but the sealant coating resolution is not reached, the notification is prompted to declare the failure of the sealant coating process.

Figure 3:
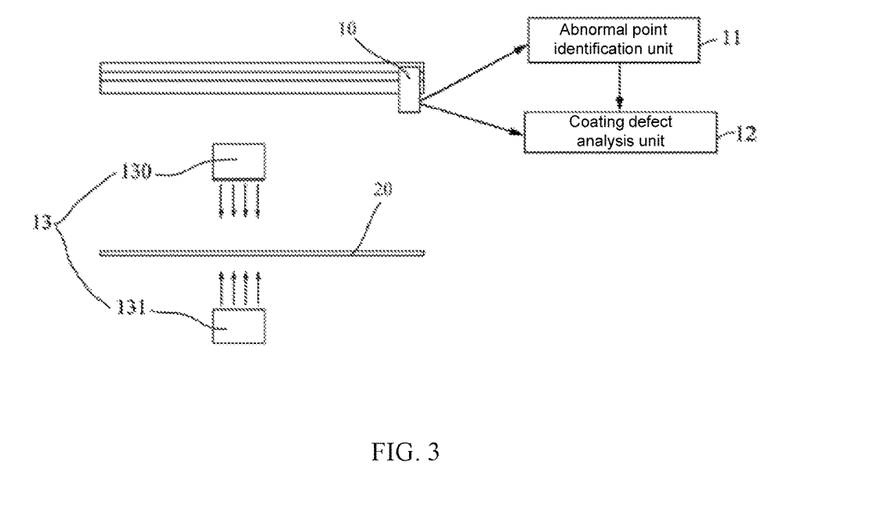
FIG. 3 illustrates a schematic view of an exemplary device of inspecting a sealant coating according to an exemplary embodiment of the present disclosure.

FIG. 3 illustrates a schematic view of an exemplary device of inspecting the sealant coating. As shown in FIG. 3, the sealant coating inspection device includes an image acquisition unit 10, an abnormal-point identification unit 11, and a coating defect analysis unit 12.

The image acquisition unit 10 is configured to capture the images of un-coated sample substrates and the images of sealant-coated substrates. For example, the image acquisition unit 10 may include a CCD camera. In one embodiment, the image acquisition unit may further include an optical wave-plate, a controllable optical grating lens, a light source, an optical circulator, an optical filter, and/or a controllable camera lens.

The abnormal-point identification unit 11 is configured to identify abnormal points such as fake sealant drops in the non-coating area and to record the positions of fake sealant drops.

The coating defect analysis unit 12 is configured to analyze the images of the sealant-coated substrates, to identify the sealant coating defects, and to ignore the defects located at the positions of the fake sealant drops. For example, the coating defect analysis unit 12 may be configured to identify defect positions of a sealant coating from an image of a sealant-coated substrate having the sealant coating on any one substrate of the batch of substrates. Defects located in a non-coating area of the sealant-coated substrate at positions corresponding to the positions of the abnormal points identified based on the sample substrate are then considered as normal and may be ignored during the inspection.

In addition, the sealant coating inspection device also includes light sources 13. The light sources 13 illuminate the substrate 20. Preferably, the light sources 13 include a first light source component 130 and a second light source component 131. The first light source component 130 and the second light source component 131 are configured on both sides of the substrate 20. Such configuration enhances the brightness and contrast of the substrate 20 and avoids the highlighted areas of intense brightness. Thus, the mark points, actual sealant-coated area and the patterns of other structures in the images captured by the image acquisition unit 10 are easy to identify and the contours of the patterns of the structures are recognized more precisely.

Specifically, the sealant coating inspection device also includes a light source monitoring unit, configured to measure and monitor the light intensity of the light sources 13. The light intensity of the light sources 13 degrades over time. Aged light sources 13 may be replaced when the light intensity thereof decreases below certain threshold. Further, the light source monitoring units are configured on the output sides of the first light source component 130 and the second light source component 131.

The sealant coating inspection device also includes a transmittance monitoring unit, configured to measure and monitor the lens surface transmittance of the image acquisition unit 10. When the lens surface transmittance fluctuates, for example, the lens surface is contaminated with dust, proper action may be taken promptly to correct the problem.

The present disclosure provides a sealant coating inspection device. Before the substrates 20 are coated with the sealant, the abnormal-point identification unit 11 identifies abnormal points such as fake sealant drops in the non-coating area. The abnormal points such as fake sealant drops may trigger false defect identifications in the subsequent process. After the substrates 20 are coated with the sealant material, the coating defect analysis unit 12 analyzes the sealant-coated substrate images to identify any sealant coating defects. Defects located at the positions of the fake sealant drops are ignored. The chance of false defect identifications is reduced in the sealant coating inspection. The precision and reliability of the sealant coating inspection results are improved. In the meantime, the reduction in false defect identifications reduces the chance of disruptions to the sealant coating production line and avoids unnecessary adjustments to the sealant coating process conditions. Thus, the productivity of the sealant coating production line is improved.

In another embodiment, the sealant coating inspection device includes a pre-treatment control system for the sealant coating image analysis and the mark point identification. The pre-treatment control system includes a CCD system configuration unit, a mark point configuration unit, an imaging system configuration unit, a light source system configuration unit, a light source parameter configuration unit, image processing unit, a coating platform control unit, and a status recording unit.

The CCD system configuration unit is used to configure coating platform parameters and CCD detection parameters per movement axis based on the known CCD system mechanical structure. The CCD detection parameters per movement axis require adjustments through multiple iterations of sealant coating simulation, per axis movement tracking and time measurements. The parameters may be finalized after multiple test runs. This step provides useful references to rapidly configure CCD system parameters and to reduce on-site commissioning time.

The mark point configuration unit is used to configure the number of mark points based on the number of CCD cameras, to configure the positions of each mark point, and to configure the parameters of the pattern of the mark points, such as the detection condition and size. The alignment pattern of the mark points is stored in this unit. The deviation between the position of the identified mark point from the substrate images and the position of the mark point stored in this unit is calculated to determine the movement distance required for each axis of the coating platform.

The imaging system configuration unit is used to configure the focus and lens surface transmittance of each camera to compensate the performance degradation due to camera aging. The focus parameter ranges from about 0 to about 1. The number "0" herein represents totally out of focus. The number "1" herein represents perfect focus. The focus parameter affects the image quality. For example, out of focus means blurred images. The CCD lens surface transmittance parameter may be entered through mouse pointer selection or keyboard typing. The lens surface transmittance parameter ranges approximately from about 0 to about 1. Herein, "0" represents no light passes through the lens surface. "1" represents all light passes through the lens surface. The lens surface transmittance parameter affects the image quality. For example, the images may have random scratches and dots, background noises in certain portion of the image, and a portion of image missing.

The light source system configuration unit is used to configure the change of the light intensity of the light source to compensate the light intensity decrease due to light source aging. The light intensity of the light source parameter ranges approximately from about 0 to about 255. The number "0" herein represents no light from the light source. The larger number represents the stronger light intensity of the light source. The light intensity of the light source parameter affects image quality. For example, the images may be too dark, or clear, or too bright.

The light source parameter configuration unit is used to configure light source dust and light source light intensity to take into account of the on-site light sources. The light source dust parameter ranges approximately from about 0 to about 1. The number "0" herein represents no dust. The number "1" herein represents maximum dust. The larger number represents thicker dust. The light source dust parameter affects the image quality. For example, the images may be clear or noisy. The light intensity parameter of the light source ranges approximately from about 0 to about 20. The number "0" herein represents no light from the light source. The number "20" herein represents the maximum light source light intensity. The larger number represents brighter light source. The light source light intensity parameter affects the image quality. For example, the images may be too dark, or clear, or too bright.

The image processing unit is used to acquire images, to process images, to identify mark points, and to calculate the deviation between the center coordinate of detected mark point and the stored position of the mark point to determine the movement distance per axis of the coating platform and the completion of the coating operation.

The coating platform control unit is used to control the movement of the coating platform based on the calculated movement distance per axis of the coating platform to complete the coating operation.

The status recoding unit is used to record the movement trajectory, the duration of the movement, and the sealant coating cross sectional area threshold for declare the completion of the coating operation. The recorded data may be used by engineers as references to optimize the CCD system configuration parameters.

Figure 4:
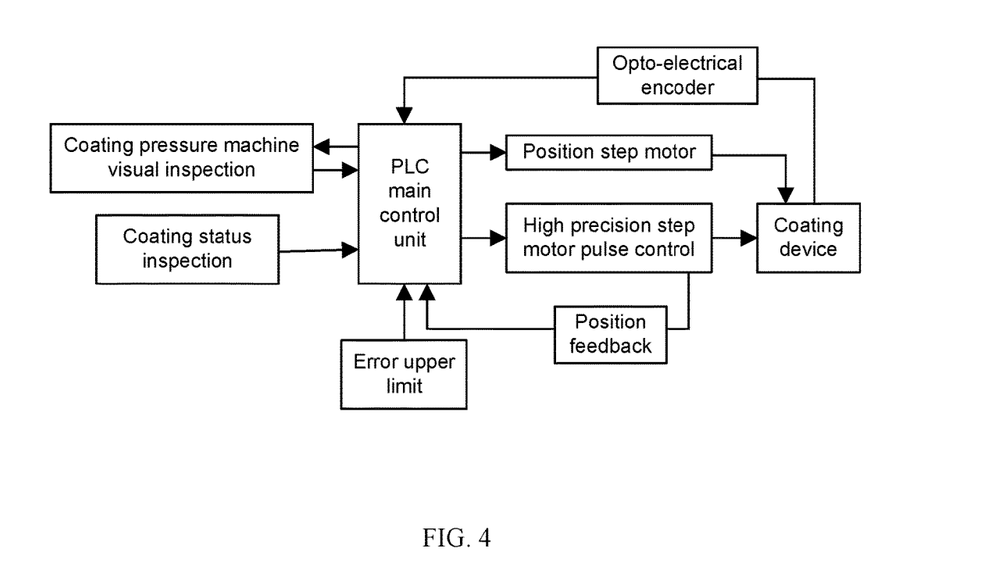
FIG. 4 illustrates a block diagram of an exemplary control system of a coating device according to an exemplary embodiment of the present disclosure.

FIG. 4 illustrates a block diagram of an exemplary control system of a coating device. The control system includes a main control unit, configured to process input data and control the step motor to move the coating device. The main control unit collects coating pressure data, coating status data, coating device data and step motor position feedback data. For example, the collected data may be used to control the step motor to adjust the distance between the nozzle and the substrate, to adjust the nozzle pressure, to adjust the step motor pulses, to control the sealant flow rate, and to adjust the coating platform position. The main control unit also takes configuration data such as error upper limit. In addition to controlling the step motor, the main control unit also controls the inspection camera.

Figure 5:
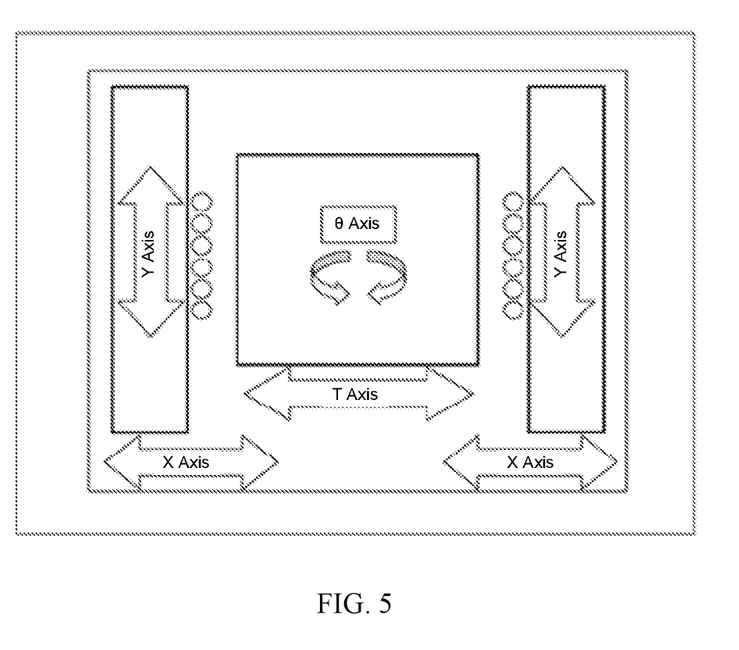
FIG. 5 illustrates a schematic diagram of three dimensional movement of an exemplary coating platform according to an exemplary embodiment of the present disclosure.

FIG. 5 illustrates a schematic diagram of three dimensional movement of an exemplary coating platform. Attached to the coating platform, the substrate may be moved in the combination of the X axis, Y axis and theta axis.

As such, the present disclosure provides a method and device of inspecting sealant coating. Before substrates are coated with the sealant material, the sample substrate images are acquired and examined to identify the non-coating area, to identify abnormal points such as fake sealant drops in the non-coating area, and to record the positions of the identified fake sealant drops. When the sealant-coated substrate images are acquired and inspected, the coating defects located at the positions of the previously recorded fake sealant drops are ignored to reduce the chance of false defect identifications and to improve the precision and reliability of the coating inspection results. In the meantime, the reduction of the false defect identifications reduces disruptions and unnecessary human interventions to the sealant coating production line and improves the productivity of the sealant coating production line.

The embodiments disclosed herein are exemplary only. Other applications, advantages, alternations, modifications, or equivalents to the disclosed embodiments are obvious to those skilled in the art and are intended to be encompassed within the scope of the present disclosure.

What is claimed is:

1. A method of sealant coating inspection, comprising:
capturing an image of a sample substrate selected from a plurality of substrates;
identifying a non-coating area from the image of the sample substrate, identifying abnormal points in the non-coating area, and recording positions of the abnormal points with respect to an alignment mark, wherein the abnormal points include areas or points on the sample substrate, and, in the areas or points, brightness and contrast are similar to or comparable with brightness and contrast of a sealant coating on the sample substrate;
capturing an image of a sealant-coated substrate having the sealant coating on one of the plurality of substrates; and
identifying defect positions of the sealant coating from the image of the sealant-coated substrate, wherein defects located in a non-coating area of the sealant-coated substrate at positions corresponding to the positions of the abnormal points identified based on the sample substrate are considered as normal.

2. The method of claim 1, further comprising:
selecting a group of sample substrates from the plurality of substrates, wherein the group of sample substrates includes the sample substrate,
capturing images of the group of sample substrates,
identifying abnormal points in non-coating areas of the group of sample substrates, and
considering a combination of the abnormal points from the images of the group of sample substrates as normal for identifying the defect positions of the sealant coating of the sealant-coated substrate.

3. The method of claim 1, further including:
repeatedly capturing the image of the sample substrate to obtain a plurality of images of the sample substrate, wherein:
the abnormal points include a combination of abnormal points from each image of the plurality of images of the sample substrate.

4. The method of claim 1, prior to identifying the non-coating area from the image of the sample substrate, further including:
examining brightness and contrast of the image of the sample substrate to determine whether the brightness and the contrast is each within a pre-configured range, and
proceeding to identify the non-coating area from the image of the sample substrate, when the brightness and the contrast is each within a pre-configured range.

5. The method of claim 1, further including a light source configured on at least one side of the sample substrate or the sealant-coated sample substrate for illumination.

6. The method of claim 1, further including a light source configured on each of opposing sides of the sample substrate or the sealant-coated sample substrate for illumination.

7. The method of claim 5, further including monitoring a light intensity of the light source.

8. The method of claim 1, further including:
configuring mark points on the sample substrate, wherein:
the non-coating area is identified by examining a position of an alignment pattern containing the mark points and based on a relationship between positions of the mark points and a coating area supposed for coating the sealant material, to identify the coating area supposed for the sealant coating and the non-coating area outside of the coating area.

9. The method of claim 8, wherein at least two mark points are configured on the sample substrate.

10. The method of claim 1, wherein identifying the abnormal points in the non-coating area includes:
acquiring brightness and contrast characteristics of the sealant coating, and
comparing brightness and contrast characteristics of the image of the sample substrate in the non-coating area with the brightness and contrast characteristics of the sealant coating, wherein:
when the brightness and contrast characteristics of certain areas or points in the image of the sample substrate have substantially same brightness and contrast characteristics of the sealant coating, the certain areas or points are identified as the abnormal points.

11. A device for sealant coating inspection, comprising:
a camera, configured to capture an image of a sample substrate selected from a plurality of substrates; and
a processor, configured to
identify a non-coating area from the image of the sample substrate, identify abnormal points in the non-coating area, and record positions of the abnormal points with respect to an alignment mark, wherein the abnormal points include areas or points on the sample substrate, and, in the areas or points, brightness and contrast are similar to or comparable with brightness and contrast of a sealant coating on the sample substrate; and
identify defect positions of the sealant coating from an image of a sealant-coated substrate having the sealant coating on one of the plurality of substrates, wherein defects located in a non-coating area of the sealant-coated substrate at positions corresponding to the positions of the abnormal points identified based on the sample substrate are considered as normal.

12. The device of claim 11, further including light sources to illuminate the sample substrate or the sealant-coated substrate for inspection.

13. The device of claim 12, wherein the light sources include first light source components and second light source components, configured on opposing sides of the sample substrate or the sealant-coated substrate for inspection.

14. The device of claim 12, wherein the processor is further configured to measure and monitor a light intensity of the light sources.

15. The device of claim 11, wherein the processor is further configured to measure and monitor a lens surface transmittance of the camera.

16. The device of claim 11, wherein the processor is further configured to analyze the image of the sealant coating and to identify mark points on the sealant-coated substrate corresponding to mark points configured on the sample substrate.

17. The device of claim 16, wherein the processor comprises:
one or more selected from a CCD system configuration unit, a mark point configuration unit, an imaging system configuration unit, a light source system configuration unit, a light source parameter configuration unit, an image processing unit, a coating platform control unit, and a status recording unit.

18. A method of sealant coating inspection, comprising:
selecting a group of sample substrates from a plurality of substrates;
capturing images of the group of sample substrates;
identifying a non-coating area from each of the images of the group of the sample substrates, identifying abnormal points in the non-coating area on each of the group of sample substrates, and recording positions of a combination of the abnormal points of the group of sample substrates;
capturing an image of a sealant-coated substrate having a sealant coating on one of the plurality of substrates; and
identifying defect positions of the sealant coating from the image of the sealant-coated substrate, wherein defects located in a non-coating area of the sealant-coated substrate at positions corresponding to the positions of the combination of the abnormal points identified based on the images of the group of sample substrates are considered as normal.

* * * * *